United States Patent
Mochizuki et al.

(10) Patent No.: US 10,472,260 B2
(45) Date of Patent: Nov. 12, 2019

(54) FLUID STERILIZATION DEVICE

(71) Applicant: NIKKISO CO., LTD., Tokyo (JP)

(72) Inventors: Hiroaki Mochizuki, Hakusan (JP); Shinya Watanabe, Hakusan (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 15/973,928

(22) Filed: May 8, 2018

(65) Prior Publication Data
US 2018/0257953 A1    Sep. 13, 2018

Related U.S. Application Data

(63) Continuation of application No. PCT/JP2016/086043, filed on Dec. 5, 2016.

(30) Foreign Application Priority Data

Dec. 8, 2015  (JP) .................... 2015-239469

(51) Int. Cl.
*C02F 1/32* (2006.01)
*A61L 2/26* (2006.01)
(Continued)

(52) U.S. Cl.
CPC ............... *C02F 1/325* (2013.01); *A61L 2/10* (2013.01); *A61L 2/26* (2013.01); *A61L 9/20* (2013.01);
(Continued)

(58) Field of Classification Search
CPC .............. C02F 1/325; C02F 2201/3222; C02F 2201/3227; C02F 2201/3228;
(Continued)

(56) References Cited

U.S. PATENT DOCUMENTS 5,635,133 A * 6/1997 Glazman .................. A61L 2/10
                                                    250/432 R
5,780,860 A * 7/1998 Gadgil ..................... A61L 2/10
                                                    250/432 R
(Continued)

FOREIGN PATENT DOCUMENTS

JP          03-061982 U1    6/1991
JP          H04-055353 U1   5/1992
(Continued)

OTHER PUBLICATIONS

Opposition's Evidence cited in Japanese Office Action dated Oct. 30, 2017 in Japanese Patent 6080937, 23 pages.
(Continued)

*Primary Examiner* — Nicole M Ippolito
(74) *Attorney, Agent, or Firm* — Muncy, Geissler, Olds & Lowe, P.C.

(57) ABSTRACT

A fluid sterilization device includes: a flow passage tube having a first end and a second end opposite to the first end and defining a processing passage extending in an axial direction; a light source provided in a vicinity of the first end and radiating ultraviolet light from the first end toward the processing passage in the axial direction; and a housing that defines a straightening chamber encircling the first end from outside in a radial direction. The straightening chamber includes a communication port that serves as an inlet or an outlet for a fluid flowing in the processing passage, and communicates with the processing passage via a gap between the first end and an opposing member opposing the first end in the axial direction.

18 Claims, 9 Drawing Sheets

(51) Int. Cl.
*A61L 2/10* (2006.01)
*A61L 9/20* (2006.01)

(52) U.S. Cl.
CPC ... *A61L 2202/11* (2013.01); *C02F 2201/3222* (2013.01); *C02F 2201/3227* (2013.01); *C02F 2201/3228* (2013.01); *C02F 2303/04* (2013.01)

(58) Field of Classification Search
CPC .......... C02F 2303/04; A61L 2/10; A61L 2/26; A61L 9/20; A61L 2202/11
USPC ... 250/453.11, 454.11, 455.11, 493.1, 494.1, 250/504 R
See application file for complete search history.

(56) References Cited

U.S. PATENT DOCUMENTS

| | | | | |
|---|---|---|---|---|
| 2014/0202962 | A1* | 7/2014 | Bilenko | C02F 1/325 210/748.11 |
| 2015/0114912 | A1* | 4/2015 | Taghipour | C02F 1/325 210/748.11 |
| 2015/0129776 | A1 | 5/2015 | Boodaghians et al. | |
| 2015/0314024 | A1 | 11/2015 | Khan et al. | |
| 2018/0155215 | A1* | 6/2018 | Torii | A61L 2/10 |

FOREIGN PATENT DOCUMENTS

| | | |
|---|---|---|
| JP | 2003334547 A | 11/2003 |
| JP | 2005506180 A | 3/2005 |
| JP | 2007502200 A | 2/2007 |
| JP | 2011016074 A | 1/2011 |
| JP | 2014076422 A | 5/2014 |
| TW | I393674 B | 4/2013 |
| TW | M483275 U | 8/2014 |
| WO | WO2014/058011 A1 | 4/2014 |
| WO | WO2014/115146 A1 | 7/2014 |
| WO | WO2015/069680 A1 | 5/2015 |

OTHER PUBLICATIONS

"Hagen—Poiseuille equation," Wikipedia, retrieved from "https://en.wikipedia.org/w/index.php?title=Hagen—Poiseuille_equation &oldid=641937695," Jan. 10, 2015, 9 pages.
Office Action dated Sep. 26, 2019 in corresponding KR Application 10-2018-7016266, with English translation, 14 pages.

* cited by examiner

FLUID STERILIZATION DEVICE

RELATED APPLICATION

This application is a Continuation of co-pending International Patent Application No. PCT/JP2016/086043, filed on Dec. 5, 2016, for which priority is claimed under 35 U.S.C. § 120; and this application claims priority of Application No. 2015-239469 filed in Japan on Dec. 8, 2016 under 35 U.S.C. § 119;the entire contents of all of which are hereby incorporated by reference

BACKGROUND

1. Field of the Invention

The present invention relates to fluid sterilization devices and, more particularly, to a technology of sterilizing a fluid by irradiating the fluid with ultraviolet light.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example is a device in which an ultraviolet LED is provided on the inner wall at a pipe end of a flow passage formed by a straight metal pipe.

SUMMARY

In the aforementioned structure where the ultraviolet LED is provided at the end of the straight tube passage, an inlet or an outlet that extends in a direction intersecting the axial direction of the flow passage is provided so that a disturbance is produced in the flow of the fluid in the vicinity of the inlet or the outlet. In order to irradiate the fluid with ultraviolet light with a high efficiency, it is desired that the state of flow in the flow passage be controlled properly and the ultraviolet light is radiated in a mode suited to the state of flow.

In this background, one illustrative purpose of the present invention is to provide a fluid sterilization device in which the efficiency of irradiating the fluid flowing in the flow passage with ultraviolet light is increased.

A fluid sterilization device according to an embodiment of the present invention comprises: a flow passage tube having a first end and a second end opposite to the first end and defining a processing passage extending in an axial direction; a light source provided in a vicinity of the first end and radiating ultraviolet light from the first end toward the processing passage in the axial direction; and a housing that defines a straightening chamber encircling the first end from outside in a radial direction. The straightening chamber includes a communication port that serves as an inlet or an outlet for a fluid flowing in the processing passage and communicates with the processing passage via a gap between the first end and an opposing member opposing the first end in the axial direction.

As compared with the case of providing the communication port directly in the flow passage tube, the provision of the straightening chamber around the first end according to the embodiment mitigates the disturbance produced in the processing passage more successfully than and so straightens the flow in the processing passage more successfully. In particular, the disturbance is inhibited from being produced in the vicinity of the first end close to the light source so that the flow is straightened accordingly. According to this embodiment, the flow in the vicinity of the first end close to the light source is straightened and irradiated with ultraviolet light of high intensity. Therefore, the sterilization efficiency is increased.

At least a portion of the opposing member may be made of a material that transmits the ultraviolet light from the light source and the light source may be provided in a light source chamber defined by the housing and the opposing member.

The opposing member may be provided such that a dimension of the gap in the axial direction is uniform over an entire circumference of the first end.

The fluid sterilization device may further comprise a connecting pipe connected to the communication port. The connecting pipe may extend in a direction. intersecting a direction from the gap toward the communication port.

The communication port may be provided at a position shifted from the gap in the axial direction.

The straightening chamber may have a section that extends outside the fluid passage tube from the first end toward the second end in the axial direction.

The fluid passage tube may be made of a material that reflects the ultraviolet light from the light source.

The housing may be made of a material having a lower reflectivity for the ultraviolet light than the flow passage tube.

The flow passage tube may have a projection that projects radially inward from the first end.

The light source may include at least one light emitting device that emits ultraviolet light and radiates ultraviolet light in a light distribution in which an ultraviolet light intensity near a center of a cross-section of the processing passage perpendicular to the axial direction is higher than an ultraviolet light distribution toward a circumference.

The light source may be arranged such that an entirety of the ultraviolet light output from the light source in a range of half-power beam width is incident into the processing passage.

The fluid sterilization device may further comprise a straightener for straightening the fluid flowing in the processing passage.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Described below is an explanation of the embodiments of the present invention with reference to figures. In the figures, like numerals represent like constituting elements, and the description thereof is omitted appropriately.

A description will be given of the embodiments of the present invention with reference to the drawings. Like numerals are used in the description to denote like elements and the description is omitted as appropriate.

First Embodiment

Figure 1:
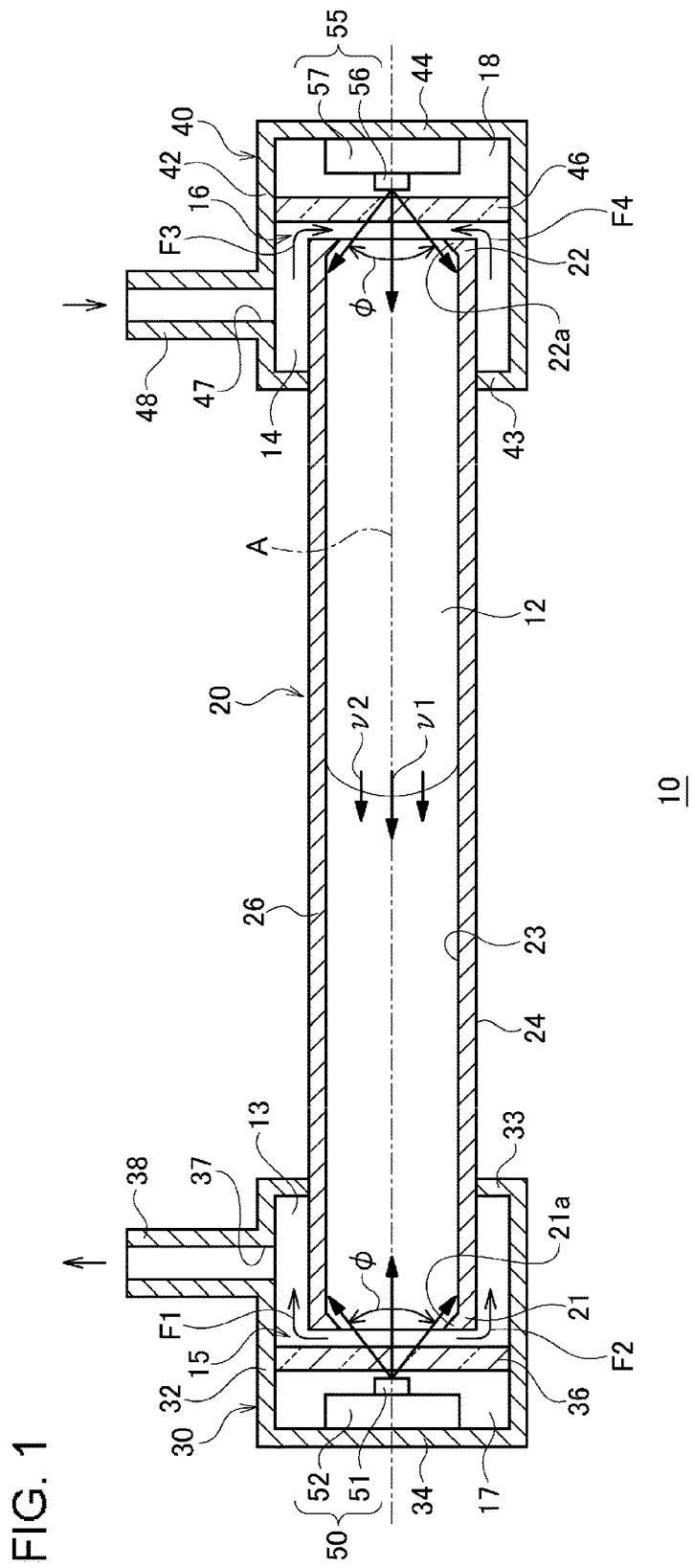
FIG. 1 is a cross-sectional view schematically showing a configuration of a fluid sterilization device according to the first embodiment.

FIG. 1 schematically shows a configuration of a fluid sterilization device 10 according to the first embodiment. The fluid sterilization device 10 includes a flow passage tube 20, a first housing 30, a second housing 40, a first light source 50, and a second light source 55. The first light source 50 and the second light source 55 radiate ultraviolet light toward the interior of the flow passage tube 20. The fluid sterilization device 10 is used to irradiate the fluid (water etc.) flowing in the flow passage tube 20 with ultraviolet light so as to sterilize the fluid.

In this specification, the longitudinal direction of the flow passage tube 20 may be referred to as "axial direction" to facilitate understanding. For example, referring to FIG. 1, the direction parallel to the central axis A is the axial direction. The direction perpendicular to the axial direction may be referred to as the radial direction and the direction encircling the axial direction may be referred to as the circumferential direction. With reference to the positions at the ends (a first end 21 and a second end 22) of the flow passage tube 20, the direction toward the interior of the flow passage tube 20 may be referred to as "inward" and the direction toward the outside of the flow passage tube 20 may be referred to as "outward".

The flow passage tube 20 is a straight tube comprised of a cylindrical side wall 26. The flow passage tube 20 has a first end 21 and a second end 22 opposite to the first end 21 and extends in the axial direction from the first end 21 to the second end 22. Ultraviolet light from the first light source 50 is incident on the first end 21 and ultraviolet light from the second light source 55 is incident on the second end 22. The flow passage tube 20 defines a processing passage 12 in which a fluid is irradiated with ultraviolet light.

The flow passage tube 20 is made of a metal material or a resin material. The flow passage tube 20 is desirably made of a material having a high ultraviolet reflectivity. For example, an inner surface 23 is made of mirror-polished aluminum (Al) or polytetrafluoroethylene (PTFE), which is a fully fluorinated resin. By forming the flow passage tube 20 using a material like the above, the ultraviolet light emitted by the first light source 50 and the second light source 55 can be reflected by the inner surface 23 to propagate in the longitudinal direction of the flow passage tube 20. In particular, PTFE is a chemically stable material and has a high ultraviolet reflectivity for ultraviolet light and so is suitable as the material for the flow passage tube 20 forming the processing passage 12.

The flow passage tube 20 includes a first projection 21a projecting radially inward from the first end 21 and a second projection 22a projecting radially inward from the second end 22. The first projection 21a and the second projection 22a are formed on the entire circumference of the first end 21 or the second end 22 and are shaped to reduce the inner diameter of the flow passage tube 20. The first projection 21a and the second projection 22a may be shaped such that the amount of projection in the radial direction varies progressively in the axial direction. The first projection 21a and the second projection 22a may have a triangular cross-sectional shape in the illustrated cross-section including the central axis A.

The first projection 21a and the second projection 22a are formed in a range that does not block the incidence of the ultraviolet light directly output from the first light source 50 or the second light source 55. For example, the first projection 21a and the second projection 22a are formed so as not to block the ultraviolet light in the range of half-power beam width φ of the first light source 50 or the second light source 55. By providing the first projection 21a and the second projection 22a, a portion of the ultraviolet light reflected or scattered by the inner surface 23 of the flow passage tube 20 and traveling toward the outside of the flow passage tube 20 is reflected by the first projection 21a or the second projection 22a and returned to interior of the flow passage tube 20.

The first housing 30 is provided to encircle the first end 21 and defines a first straightening chamber 13 and a first light source chamber 17. The first housing 30 is made of a metal material or a resin material. It is desirable that the first housing 30 be made of a material having a low reflectivity for the ultraviolet light emitted by the first light source 50 and be made of a material having a lower ultraviolet reflectivity than the flow passage tube 20. The first housing 30 may be made of a material that absorbs the ultraviolet light from the first light source 50. By configuring the first housing 30 by using a material like the above, the ultraviolet light from the first light source 50 is inhibited from being reflected by the inner surface of the first housing 30 and leaking outside via an outflow pipe 38.

The first housing 30 has a first side wall 32, a first inner end wall 33, and a first outer end wall 34. The first side wall 32 is a cylindrical member extending from the first inner end wall 33 to the first outer end wall 34 in the axial direction and is provided at a position coaxial with the central axis A of the flow passage tube 20. The first inner end wall 33 is a member extending radially outward from the side wall 26 of the flow passage tube 20 to the first side wall 32 and has an annular shape (doughnut shape). The first inner end wall 33 is provided at a position axially inward from the first end 21 and is fixed to an outer surface 24 of the flow passage tube 20. The first outer end wall 34 is a disc-shaped member provided at a position axially outward from the first end 21. Therefore, the first inner end wall 33 and the first outer end wall 34 are provided at positions axially opposite to each other, sandwiching the first end 21.

A first window 36 for transmitting the ultraviolet light from the first light source 50 is provided inside the first housing 30. The first window 36 is made of a material having a high ultraviolet transmittance such as quartz (SiO2), sapphire (Al2O3), and amorphous fluororesin. The first window 36 partitions the interior of the first housing 30 into the first straightening chamber 13 and the first light source chamber 17. The first straightening chamber 13 is an area defined by the first side wall 32, the first inner end wall 33, and the first window 36 and is an area provided annularly to encircle the first end 21 from outside in the radial direction. The first light source chamber 17 is an area defined by the first side wall 32, the first outer end wall 34, and the first window 36 and is provided with the first light source 50.

The first window 36 is an opposing member that opposes the first end 21 in the axial direction and is provided in the vicinity of the first end 21 so as to provide a first gap 15 of a small dimension relative to the first end 21. For example, the first gap 15 is formed to be narrower than the cross-sectional area of flow of the processing passage 12 and the first straightening chamber 13. It is preferable that the first window 36 be provided such that the dimension of the first gap 15 is uniform over the entire circumference of the first end 21. It is also preferable that the end face of the first end 21 and the opposing face of the first window 36 are substantially parallel. Configuring the first gap 15 to be uniform over the entire circumference straightens the flow of the fluid traveling from the processing passage 12 to the first straightening chamber 13 via the first gap 15 and mitigates the disturbance produced in the flow in the vicinity of the first end 21 of the processing passage 12.

The first housing 30 is provided with an outflow port 37 and an outflow pipe 38. The outflow port 37 is a communication port through which the fluid irradiated with ultraviolet light in the processing passage 12 flows out and is provided at a position communicating with the first straightening chamber 13. For example, the outflow port 37 is provided in the first side wall 32 as illustrated. The outflow pipe 38 is a connecting pipe fitted to the outflow port 37 and is configured such that a pipe or a tube connector for connection to the fluid sterilization device 10 can be mounted.

The outflow port 37 and the outflow pipe 38 are arranged such that the direction from the first gap 15 toward the outflow port 37 and the longitudinal direction of the outflow pipe 38 are not on the same straight line. More specifically, the outflow port 37 is located at a position shifted from the first gap 15 in the axial direction, and the outflow pipe 38 extends in a direction (the radial direction, in the illustrated example) intersecting the direction from the first gap 15 toward the outflow port 37. This arrangement mitigates the impact of variation in the flow rate depending on the position in the circumferential direction of the first gap 15. More specifically, the arrangement mitigates the impact of the flow F1 of the fluid flowing in the first gap 15 at a position relatively near the outflow port 37 being faster and the flow F2 at a position relatively far from the outflow port 37 being slower due to the direction of the flow in the outflow pipe 38.

The first light source 50 is provided inside the first light source chamber 17 and is arranged to output ultraviolet light toward the opening of the first end 21. It is preferable that the first light source 50 be provided in the vicinity of the first end 21 and be arranged such that the entirety of the ultraviolet light in the range of half-power beam width φ of the first light source 50 is incident into the processing passage 12. More specifically, denoting the distance from the light emission part of the first light source 50 to the first end 21 by l, and denoting the diameter of the opening of the first end 21 by d, it is preferable that the first light source 50 be arranged such that $l \leq d/(2 \tan(\varphi/2))$.

The light source 50 includes a first light emitting device 51 and a first substrate 52. The first light emitting device 51 is a light emitting diode (LEDs) configured to emit ultraviolet light, and the central wavelength or peak wavelength thereof is included in a range of about 200 nm~350 nm. It is preferable that the first light emitting device 51 emit ultraviolet light near a wavelength range of 260 nm~290 nm having a high sterilizing efficiency. Such an ultraviolet LED is exemplified by an aluminum gallium nitride (AlGaN) based LED.

Figure 2:
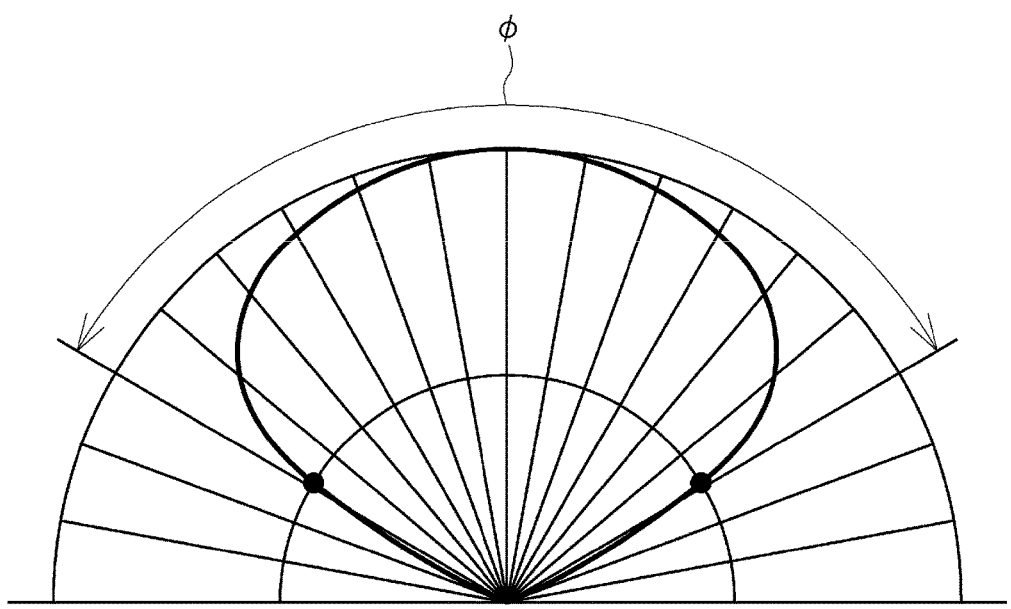
FIG. 2 is a graph showing the light distribution characteristic of the light emitting device.

FIG. 2 is a graph showing the light distribution characteristic of the first light emitting device 51. The first light emitting device 51 is an LED having a predetermined directivity angle or light distribution angle. As shown in the figure, the first light emitting device 51 is a wide light-distribution LED characterized by a half-power beam width φ of about 120°. The first light emitting device 51 with such a specification is exemplified by a surface mount device (SMD) type LED characterized by a high output intensity. The first light emitting device 51 is arranged on the central axis A of the flow passage tube 20 and is mounted on the first substrate 52 so as to oppose the first window 36. The first substrate 52 is made by using a highly exoergic member. For example, copper (Cu), aluminum (Al), or the like is used as a base material. The heat generated by the first light emitting device 51 is dissipated via the first substrate 52.

The second housing 40 is configured similarly to the first housing 30. The second housing 40 is provided to encircle the second end 22 and defines a second straightening chamber 14 and a second light source chamber 18. The second housing 40 has a second side wall 42, a second inner end wall 43, and a second outer end wall 44.

The second side wall 42 is a cylindrical member extending from the second inner end wall 43 to the second outer end wall 44 in the axial direction and is provided at a position coaxial with the central axis A of the flow passage tube 20. The second inner end wall 43 is an annular member provided at a position axially inward from the second end 22 and is fixed to the outer surface 24 of the flow passage tube 20. The second outer end wall 44 is a disc-shaped member provided at a position axially outward from the second end 22. The second inner end wall 43 and the second outer end wall 44 are provided at positions axially opposite to each other, sandwiching the second end 22.

A second window 46 for transmitting the ultraviolet light from the second light source 55 is provided inside the second housing 40. The second window 46 partitions the interior of the second housing 40 into the second straightening chamber 14 and the second light source chamber 18. The second straightening chamber 14 is an area defined by the second side wall 42, the second inner end wall 43, and the second window 46 and is an area provided annularly to encircle the second end 22 from outside in the radial direction. The second light source chamber 18 is an area defined by the second side wall 42, the second outer end wall 44, and the second window 46 and is provided with the second light source 55.

The second window 46 is a member that opposes the second end 22 in the axial direction and is provided in the vicinity of the second end 22 so as to provide a second gap 16 of a small dimension relative to the second end 22. For example, the second gap 16 is formed to be narrower than the cross-sectional area of flow of the processing passage 12 and the second straightening chamber 14. It is preferable that the second window 46 be provided such that the dimension of the second gap 16 is uniform over the entire circumference of the second end 22. It is also preferable that the end face of the second end 22 and the opposing face of the second window 46 are substantially parallel.

The second housing 40 is provided with an inflow port 47 and an inflow pipe 48. The inflow port 47 is a communication port through which the fluid irradiated with ultraviolet light in the processing passage 12 flows in and is provided at a position communicating with the second straightening chamber 14. The inflow pipe 48 is is a connecting pipe fitted to the inflow port 47. The inflow port 47 and the inflow pipe 48 are arranged such that the direction from the second gap 16 toward the inflow port 47 and the longitudinal direction of the inflow pipe 48 are not on the same straight line. More specifically, the inflow port 47 is located at a position shifted from the second gap 16 in the axial direction, and the inflow pipe 48 extends in a direction (the radial direction, in the illustrated example) intersecting the direction from the second gap 16 toward the inflow port 47. The arrangement mitigates the impact of the flow F3 of the fluid flowing in the second gap 16 at a position relatively near the inflow port 47 being faster and the flow F4 at a position relatively far from the inflow port 47 being slower due to the direction of the flow in the inflow pipe 48.

The second light source 55 is arranged inside the second light source chamber 18 and is arranged to output ultraviolet light toward the opening of the second end 22. As in the case of the first light source 50, it is preferable that the second light source 55 be provided in the vicinity of the second end 22 and be arranged such that the entirety of the ultraviolet light in the range of half-power beam width φ of the second light source 55 is incident into the processing passage 12. The second light source 55 is configured similarly to the first light source 50 and includes a second light emitting device 56 and a second substrate 57.

With the above-described configuration, the fluid sterilization device 10 irradiates the fluid flowing in the processing passage 12 with the ultraviolet light from the first light source 50 and the second light source 55 so as to sterilize the fluid. The fluid subject to the treatment flows from the second end 22 into the processing passage 12 via the inflow pipe 48, the inflow port 47, the second straightening chamber 14, and the second gap 16. The fluid flowing in the processing passage 12 is straightened such that, for example, the flow rate v1 near the center of the cross-section perpendicular to the axial direction is relatively high and the flow rate v2 near the inner surface 23 is relatively low. The fluid passing through the processing passage 12 flows out from the first end 21 via the first gap 15, the first straightening chamber 13, the outflow port 37, and the outflow pipe 38.

In this process, the second straightening chamber 14 straightens the flow of the fluid flowing in via the inflow pipe 48 and the inflow port 47 and configures the flow of the fluid flowing into the processing passage 12 in a radial fashion (radially inward) from different circumferential positions via the second gap 16 to be uniform. By configuring the flow in the second gap 16 to be uniform, the second straightening chamber 14 straightens the flow from the position in the vicinity of the second end 22 to the processing passage 12. Similarly, the first straightening chamber 13 straightens the flow of the fluid flowing out via the outflow port 37 and the outflow pipe 38 and configures the flow of the fluid flowing out from the processing passage 12 in a radial fashion (radially outward) via the first gap 15 to be uniform. By configuring the flow in the first gap 15 to be uniform, the first straightening chamber 13 maintains the flow in the processing passage 12 in a straightened state as far as the position in the vicinity of the first end 21.

The first light source 50 and the second light source 55 irradiates the fluid straightened as described above and flowing in the processing passage 12 with ultraviolet light. The first light source 50 and the second light source 55 have an intensity distribution as shown in FIG. 2 in which the intensity near the center is high and the intensity radially outward is low and so can radiate ultraviolet light with an intensity conforming to the flow rate distribution in the processing passage 12. In other words, the light sources can radiate high-intensity ultraviolet light near the center where the flow rate is high and radiate low-intensity ultraviolet light at positions radially outward where the flow rate is low. As a result, it is ensured that the amount of energy of ultraviolet light affecting the fluid passing through the processing passage 12 is uniform regardless of the radial position of passage of the fluid. Consequently, the entirety of the fluid flowing in the processing passage 12 is irradiated with ultraviolet light of a predetermined amount of energy or higher so that the sterilizing effect on the entirety of the fluid is increased.

Figure 3:
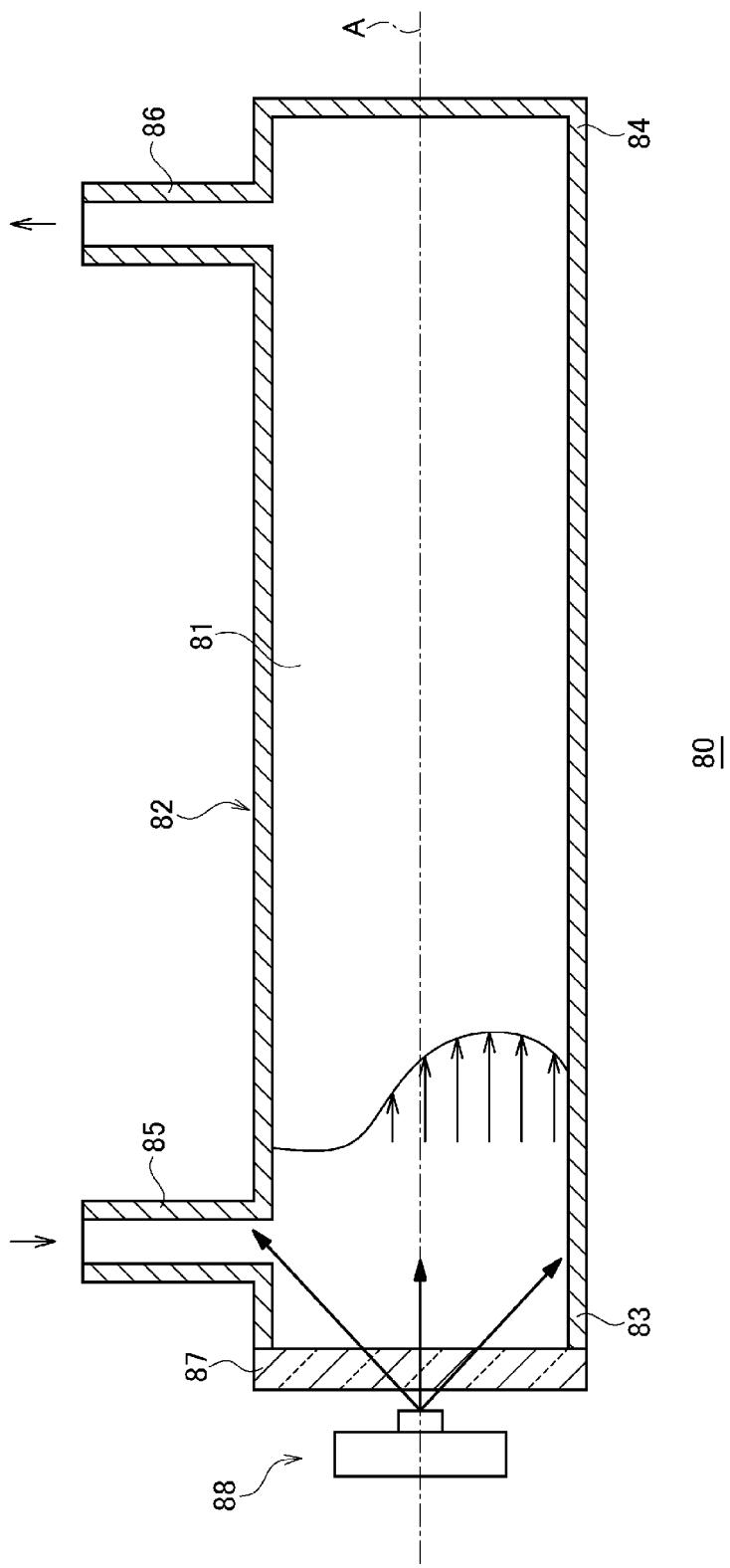
FIG. 3 is a cross-sectional diagram schematically showing a configuration of a fluid sterilization device according to a comparative example.

A description will now be given of an advantage achieved by the embodiment with reference to a comparative example. FIG. 3 shows a configuration of a fluid sterilization device 80 according to a comparative example. The fluid sterilization device 80 includes a straight tube 82 defining a processing passage 81 and a light source 88 for irradiating the interior of the straight tube 82 with ultraviolet light. The straight tube 82 has a first end 83 and a second end 84. An inflow port 85 extending in the radial direction is provided at the first end 83 and an outflow port 86 extending in the radial direction is provided at the second end 84. A window 87 for transmitting the ultraviolet light from the light source 88 is provided at the first end 83.

In the comparative example, the fluid flowing in from the inflow port 85 flows in the processing passage 81 in the axial direction and flows out from the outflow port 86. The inflow port 85 is directly provided to the side of the straight tube 82 so that a disturbance is produced in the vicinity of the first end 83. In the fluid flowing in from the inflow port 85, the flow toward the side wall of the straight tube 82 opposite to the inflow port 85 is predominant. In the interior of the processing passage 81, the speed of the fluid flowing near the side wall opposite to the inflow port 85 is relatively higher. This results in an asymmetrical speed distribution as illustrated with respect to the central axis A of the straight tube 82, which makes it difficult to cause the ultraviolet light from the light source 88 to affect the fluid efficiently. Further, the comparative example is configured such that a portion of the ultraviolet light output from the light source 88 can travel directly to the inflow port 85. Therefore, the ultraviolet light is likely to leak from the inflow port 85.

Meanwhile, according to the embodiment, the first straightening chamber 13 and the second straightening chamber 14 are provided at the respective ends of the flow passage tube 20. Therefore, the disturbance in the flow produced in the processing passage 12 can be inhibited more successfully than in the comparative example. In particular, it is easy to maintain the straightened state even when the average flow rate of the fluid flowing in the processing passage 12 is increased in order to increase the processing capability of the fluid sterilization device 10. Thus, the embodiment allows the ultraviolet light to effectively affect the fluid flowing in a less disturbed state than in the related art, thereby increasing the sterilization effect.

According to the embodiment, the majority of the ultraviolet light output from the first light source 50 and the second light source 55 is incident on the interior of the flow passage tube 20, and the ultraviolet light incident on the interior of the flow passage tube 20 propagates in the axial direction, repeatedly reflected by the inner surface 23 of the flow passage tube 20. Consequently, the ultraviolet light output from the first light source 50 and the second light source 55 can be efficiently used to increase the sterilization efficiency. Further, the projections 21a and 22a are provided in the first end 21 and the second end 22 in a range that does not block the incidence of the ultraviolet light, ensuring that a larger portion of the ultraviolet light is contained inside the flow passage tube 20 than in the related art the efficiency of using the ultraviolet light is increased.

According to the embodiment, the majority of the ultraviolet light output from the first light source 50 and the second light source 55 is contained inside the flow passage tube 20 so that the amount of ultraviolet light leaking outside the flow passage tube 20 is reduced. Since the first housing 30 and the second housing 40 are made of a material that does not reflect ultraviolet light so much, the ultraviolet light is prevented from propagating by being reflected by the inner surface of the first housing 30 or the second housing 40 and from leaking outside the fluid sterilization device 10 via the outflow pipe 38 or the inflow pipe 48. This enhances the safety of the fluid sterilization device 10 and mitigates the impact of the resin tube, connector, etc. connected to the outflow pipe 38 and the inflow pipe 48 being irradiated with ultraviolet light and degraded accordingly.

First Variation

Figure 4:
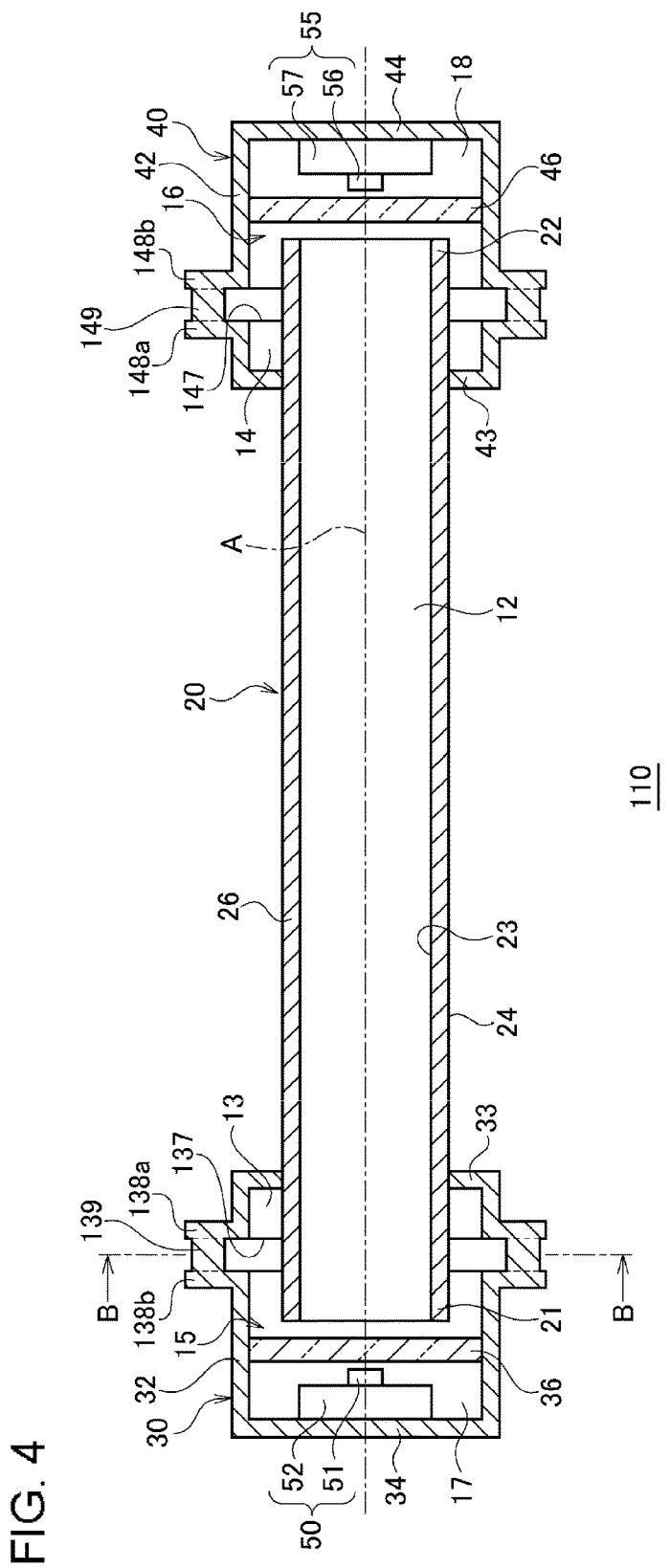
FIG. 4 is a cross-sectional view schematically showing a configuration of a fluid sterilization device according to a variation.
Figure 5:
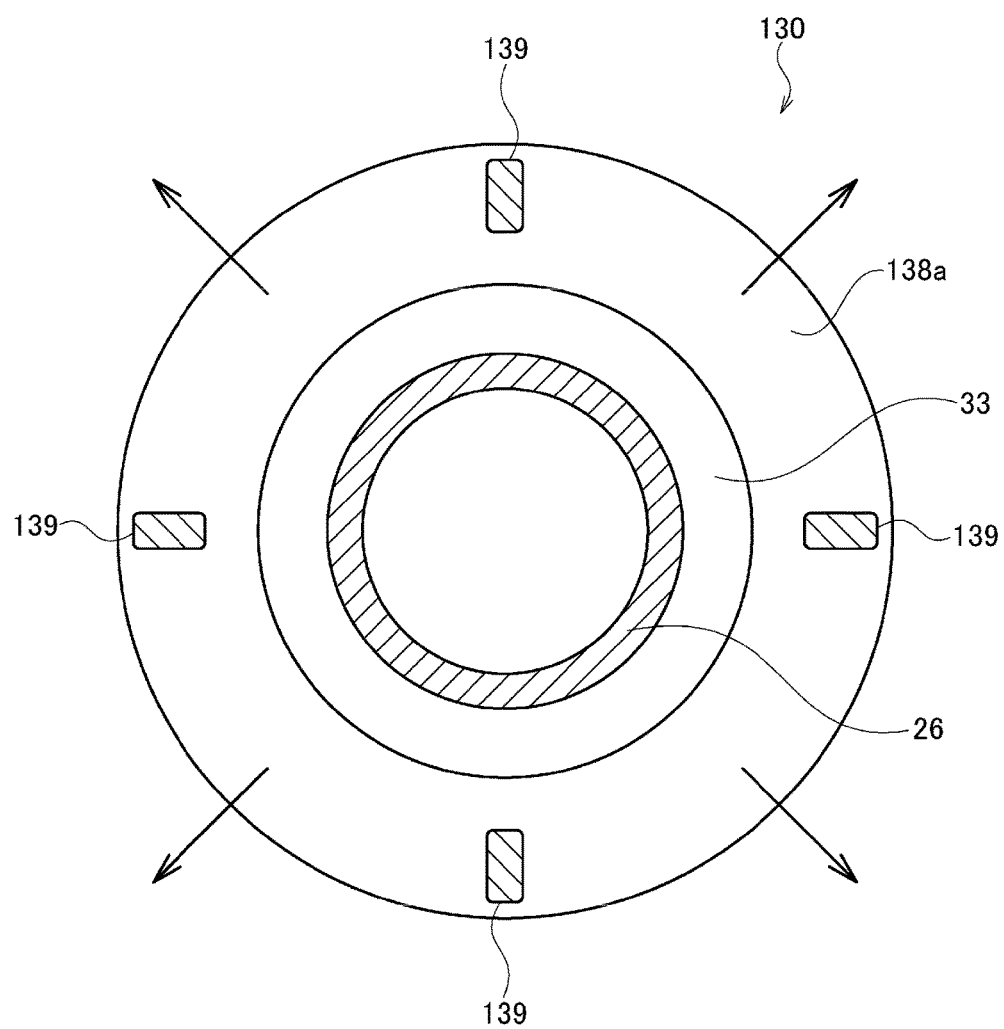
FIG. 5 is a cross-sectional view schematically showing a configuration of the fluid sterilization device shown in FIG. 4.

FIG. 4 is a cross-sectional view schematically showing a configuration of a fluid sterilization device 110 according to a first variation, and FIG. 5 shows a B-B cross-section of FIG. 4. The variation differs from the embodiment described above in that a pair of first ribs 138a and 138b projecting from the first side wall 32 of the first housing 30 in the radial direction are formed over the entire circumference of the first side wall 32, and an outflow port 137 is formed between the pair of first ribs 138a and 138b. Similarly, this variation differs from the embodiment described above in that a pair of second ribs 148a and 148b projecting from the second side wall 42 of the second housing 40 in the radial direction are formed over the entire circumference of the second side wall 42, and an inflow port 147 is formed between the pair of second ribs 148a and 148b. A description of the fluid sterilization device 110 will be given below, highlighting the difference from the fluid sterilization device 10 according to the first embodiment.

The fluid sterilization device 110 includes the flow passage tube 20, the first housing 30, the second housing 40, the first light source 50, and the second light source 55. The pair of first ribs 138a and 138b that define the outflow port 137 are formed in the first side wall 32 of the first housing 30. The pair of first ribs 138a and 138b are annular members projecting radially outward from the first side wall 32 and are opposite to each other in the axial direction. First spacers 139 for connecting the pair of first ribs 138a and 139b are provided therebetween. For example, the first spacers 139 are provided at four locations as shown in FIG. 5. The flow passage is blocked at the position where the first spacer 139 is provided, and the position where the first spacer 139 is not provided is defined as the outflow port 137.

As in the first housing 30, the pair of second ribs 148a and 148b that define the inflow port 147 are provided in the second side wall 42 of the second housing 40. The pair of second ribs 148a and 148b are annular members projecting radially outward from the second side wall 42 and are opposite to each other in the axial direction. Second spacers 149 for connecting the pair of second ribs 148a and 149b are provided therebetween. The flow passage is blocked at the position where the second spacer 149 is provided, and the position where the second spacer 149 is not provided is defined as the inflow port 147.

According to this variation, the outflow ports 137 are symmetrically arranged around the central axis A and the inflow ports 147 are symmetrically arranged around the central axis A. Therefore, the disturbance of the flow produced inside the processing passage 12 due to the asymmetrical arrangement of the outflow pipe 38 or the inflow pipe 48 is mitigated more successfully. Thus, according to this variation, the flow inside the processing passage 12 is straightened and the ultraviolet irradiation effect is further increased. In the fluid sterilization device 110, a gas such as air may be used as a fluid subject to treatment.

Second Variation

Figure 6:
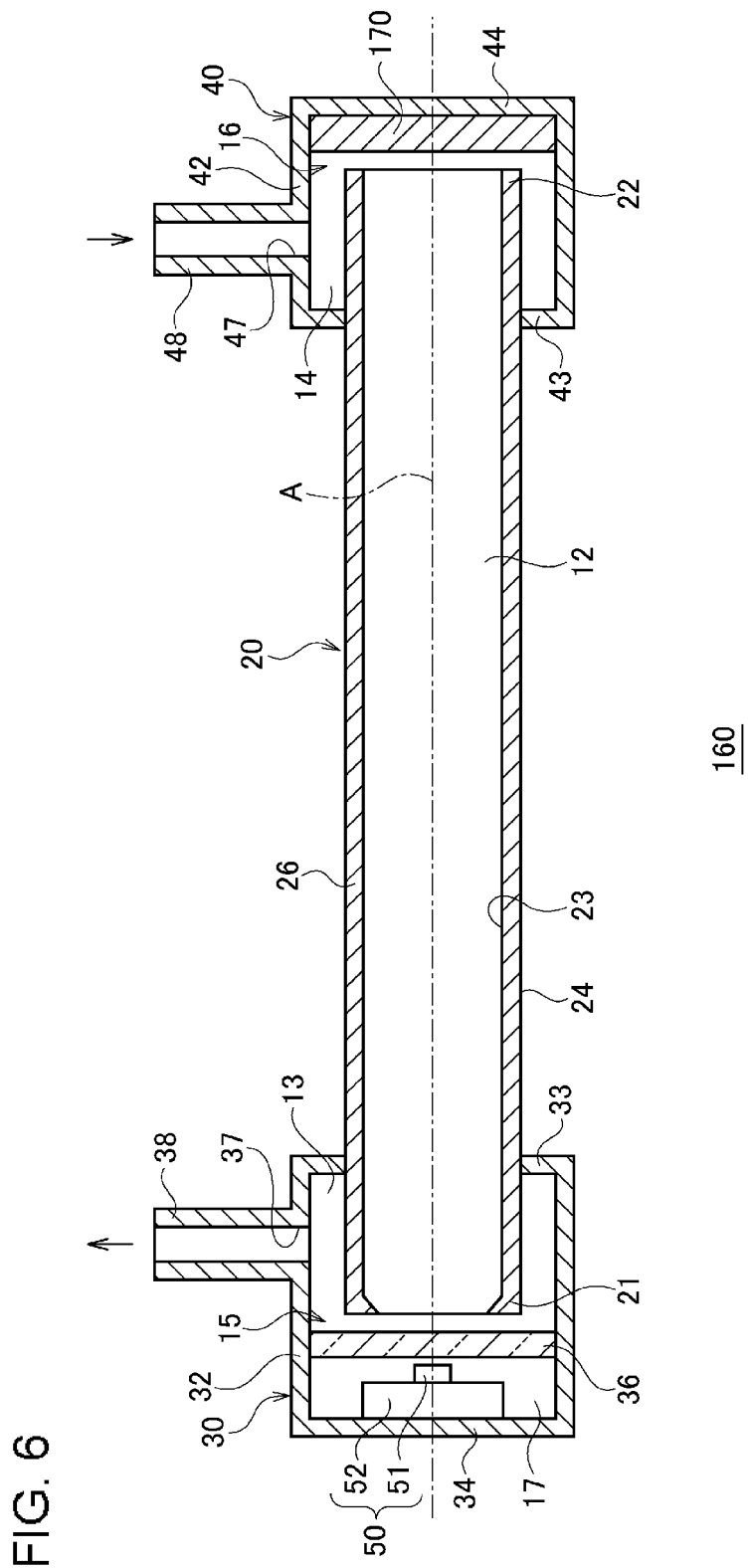
FIG. 6 is a cross-sectional view schematically showing a configuration of a fluid sterilization device according to a variation.

FIG. 6 is a cross-sectional view schematically showing a configuration of a fluid sterilization device 160 according to a second variation. This variation differs from the embodiment described above in that the second light source chamber 18 and the second light source 55 are not provided inside the second housing 40, and, instead, a reflector 170 is provided inside the second housing 40. A description of the fluid sterilization device 160 will be given below, highlighting the difference from the fluid sterilization device 10 according to the first embodiment.

The fluid sterilization device 160 includes the flow passage tube 20, the first housing 30, the second housing 40, the first light source 50, and the reflector 170. The reflector 170 is provided inside the second housing 40 at a position opposing the second end 22. The reflector 170 is made of a material having a high reflectivity for ultraviolet light and is made of, for example, mirror-polished aluminum, PTFE, etc. The reflector 170 reflects the ultraviolet light output from the first light source 50 and propagating in the flow passage tube 20 as far as the second end 22, returning the ultraviolet light to the first end 21.

The reflector 170 is an opposing member opposing the second end 22 in the axial direction and forms a second gap 16 with respect to the second end 22. It is preferable that the reflector 170 be arranged such that the dimension of the second gap 16 is uniform over the entire circumference of the second end 22, and it is also preferable that the reflector 170 be arranged in close proximity to the second end 22 such that the dimension of the second gap 16 is small. By ensuring the dimension of the second gap 16 to be small, the straightening effect of the second gap 16 is increased.

The reflector 170 may have a flat reflecting surface or a curved reflecting surface. The reflector 170 may have a concave curved surface in rotation symmetry around the central axis A or may be configured such that the ultraviolet light reflected by the reflector 170 is condensed toward the interior of the flow passage tube 20.

The reflector 170 is configured as a member separate from the second housing 40. In a further variation, the reflector 170 may be integrated with the second housing 40. Where the second housing 40 and the reflector 170 are integrated, the second outer end wall 44 may function as the reflector 170. In this case, the second outer end wall 44 is the opposing member opposing the second end 22, and the second gap 16 may be defined between the second end 22 and the second outer end wall 44.

According to this variation, despite the provision of the light source emitting ultraviolet light only at one end of the flow passage tube 20, the ultraviolet irradiation efficiency is increased as well, by providing the reflector 170 at the other end.

Second Embodiment

Figure 7:
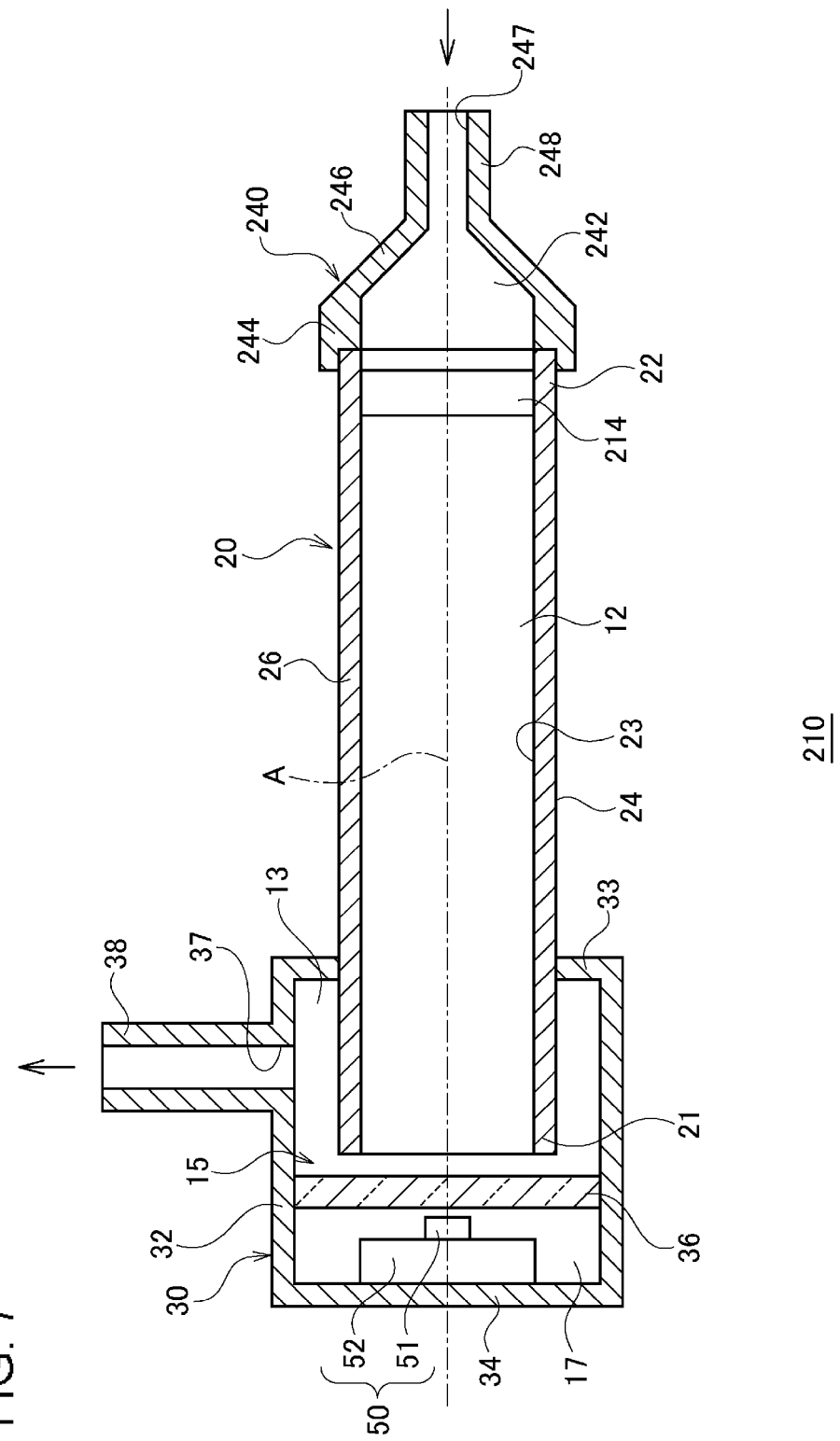
FIG. 7 is a cross-sectional view schematically showing a configuration of a fluid sterilization device according to a second embodiment.

FIG. 7 is a cross-sectional view schematically showing a configuration of a fluid sterilization device 210 according to a second embodiment. This embodiment differs from the embodiment described above in that an inflow pipe 240 is provided at the second end 22 of the flow passage tube 20 instead of providing the second housing 40. A description of the fluid sterilization device 210 will be given below, highlighting the difference from the first embodiment.

The fluid sterilization device 210 includes the flow passage tube 20, the first housing 30, the inflow pipe 240, the first light source 50, and a straightener 214. The flow passage tube 20, the first housing 30, and the first light source 50 are configured as in the first embodiment.

The inflow pipe 240 is a funnel-shaped member and connects the second end 22 with a large diameter and an inflow port 247 with a small diameter. The inflow pipe 240 has a connection end 244 connected to the second end 22, a conical part 246 having a conical shape, and a connecting pipe 248 defining the inflow port 247. The inflow pipe 240 is arranged to be coaxial with the central axis A of the flow passage tube 20 and defines an inflow passage 242 for causing the fluid flowing in via the inflow port 247 to flow toward the processing passage 12 in the axial direction. It is desirable that the inflow pipe 240 be made of a resin material or a metal material and be made of a material having a low reflectivity for ultraviolet light.

The straightener 214 is provided in the vicinity of the second end 22 and straightens the flow in the processing passage 12 by straightening the flow of the fluid flowing in via the inflow port 247. For example, the straightener 214 has a plurality of holes for allowing passage of water that extend in the axial direction of the flow passage tube 20 and places the fluid passing through the plurality of holes for allowing passage of water in a straightened state. The straightener 214 may be provided inside the flow passage tube 20 as illustrated or provided inside the inflow pipe 240.

The straightener 214 is made of a material that reflects ultraviolet light and is made of, for example, aluminum or PTFE. The straightener 214 reflects the ultraviolet light from the first light source 50 and returns the light toward the first end 21, and also shields the ultraviolet light from the first light source 50 from leaking via the inflow port 247. The straightener 214 may be configured such that the thickness of the straightener 214 in the axial direction is larger than the diameter of the holes for allowing passage of water so as to prevent the ultraviolet light from leaking via the plurality of holes for allowing passage of water.

With the above-described configuration, the fluid sterilization device 210 irradiates the fluid flowing in the processing passage 12 with the ultraviolet light from the first light source 50 so as to sterilize the fluid. The fluid subject to the treatment flows into the processing passage 12 via the inflow port 247, the inflow passage 242, and the straightener 214. The fluid irradiated with the ultraviolet light in the processing passage 12 flows out from the the first end 21 via the first gap 15, the first straightening chamber 13, the outflow port 37, and the outflow pipe 38.

According to this embodiment, the inflow pipe 140 for causing the fluid to flow in axially and the straightener 214 for straightening the flow of the fluid are provided on the inflow side, and the first straightening chamber 13 is provided on the outflow side. Therefore, the disturbance is prevented from being produced in the fluid flowing in the processing passage 12. Since the fluid flowing in the processing passage 12 in a straightened state is irradiated with the ultraviolet light having an intensity distribution conforming to the flow rate distribution, the ultraviolet light is caused to effectively affect the fluid. Thus, like the first embodiment, the embodiment increases the sterilizing effect on the entirety of the fluid.

Third Variation

Figure 8:
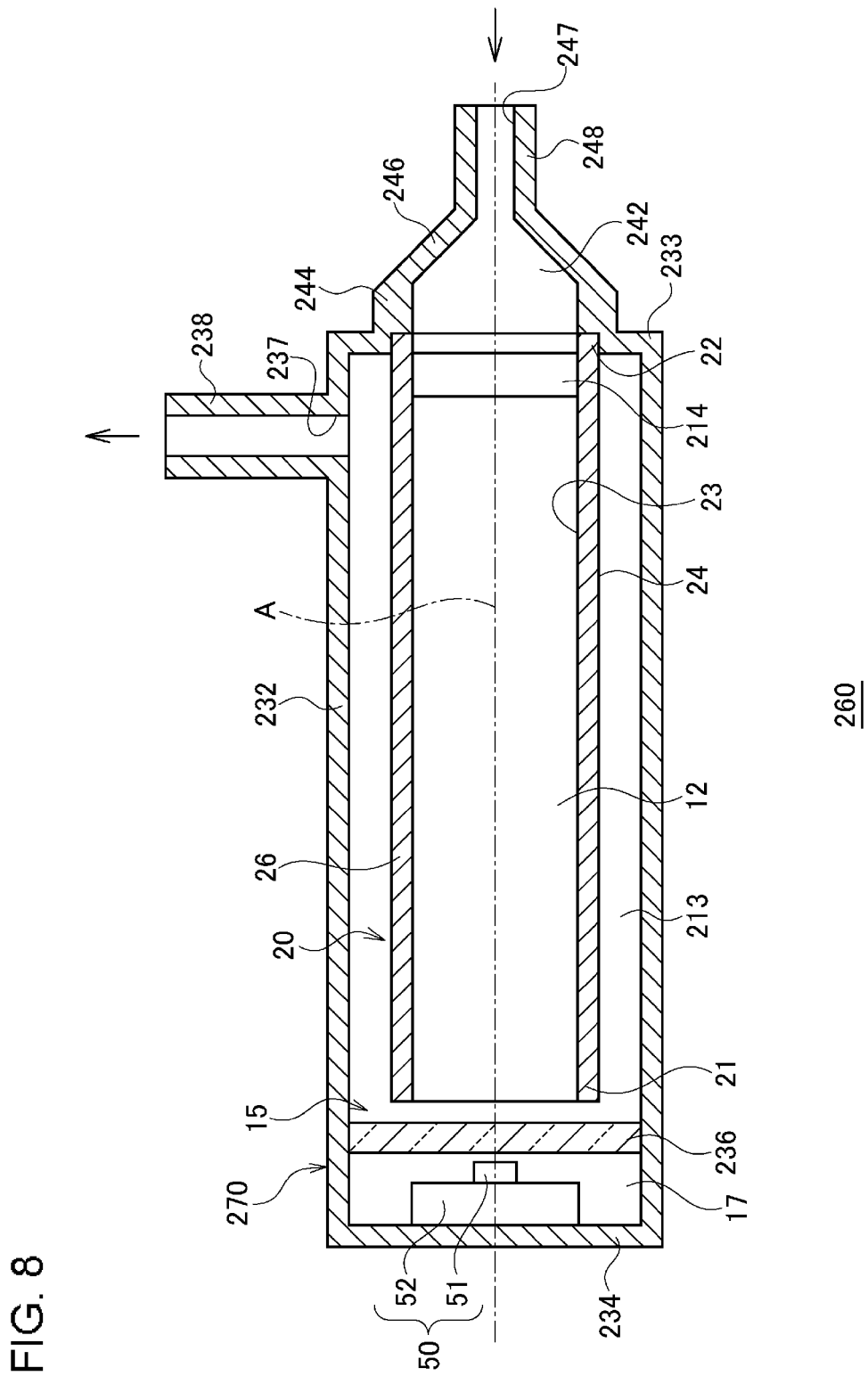
FIG. 8 is a cross-sectional view schematically showing a configuration of a fluid sterilization device according to a variation.

FIG. 8 is a cross-sectional view schematically showing a configuration of a fluid sterilization device 260 according to a third variation. This variation differs from the second embodiment described above in that a housing 270 configured by integrating the first housing 30 and the inflow pipe 240 is provided. A description will be given of the fluid sterilization device 260, highlight differences from the second embodiment.

The fluid sterilization device 260 includes the flow passage tube 20, the first light source 50, a housing 270, and the straightener 214. The housing 270 is a structure encircling the entirety of the flow passage tube 20 and is configured to define inside a dual structure of the processing passage 12 and a straightening chamber 213. The housing 270 includes a side wall 232, an inner end wall 233, an outer end wall 234, a window 236, an outflow port 237, an outflow pipe 238, the connection end 244, the conical part 246, and the connecting pipe 248.

The inner end wall 233 extends radially outward from the second end 22 or the vicinity of the second end 22 toward the side wall 232. The outer end wall 234 is provided at a position axially outward from the first end 21. The side wall 232 extends from the inner end wall 233 to the outer end wall 234 in the axial direction and is longer than the flow passage tube 20 in the axial direction. The window 236 is provided inside the housing 270 at a position opposing the first end 21.

The straightening chamber 213 is defined by the flow passage tube 20, the side wall 232, the inner end wall 233, and the window 236 and has an axial length substantially equal to that of the flow passage tube 20. Therefore, the straightening chamber 213 has a section that extends outside the flow passage tube 20 and from the first end 21 toward the second end 22 in the axial direction. The outflow port 237 is provided at a position distanced from the first end 21 in the axial direction and is provided at a position closer to the second end 22 than the first end 21. The outflow pipe 238 extends radially outward from the outflow port 237.

According to this variation, the length of the straightening chamber 213 in the axial direction is longer than in the second embodiment so that the straightening effect of the straightening chamber 213 is increased. In particular, the first end 21 and the outflow port 237 are distanced in the axial direction so that the impact from any disturbance produced in the vicinity of the outflow port 237 is inhibited from reaching the first end 21. Therefore, according to this variation, it is ensured that the flow in the processing passage 12 is even more uniform and the efficiency of irradiating the fluid with ultraviolet light is further increased.

Fourth Variation

Figure 9:
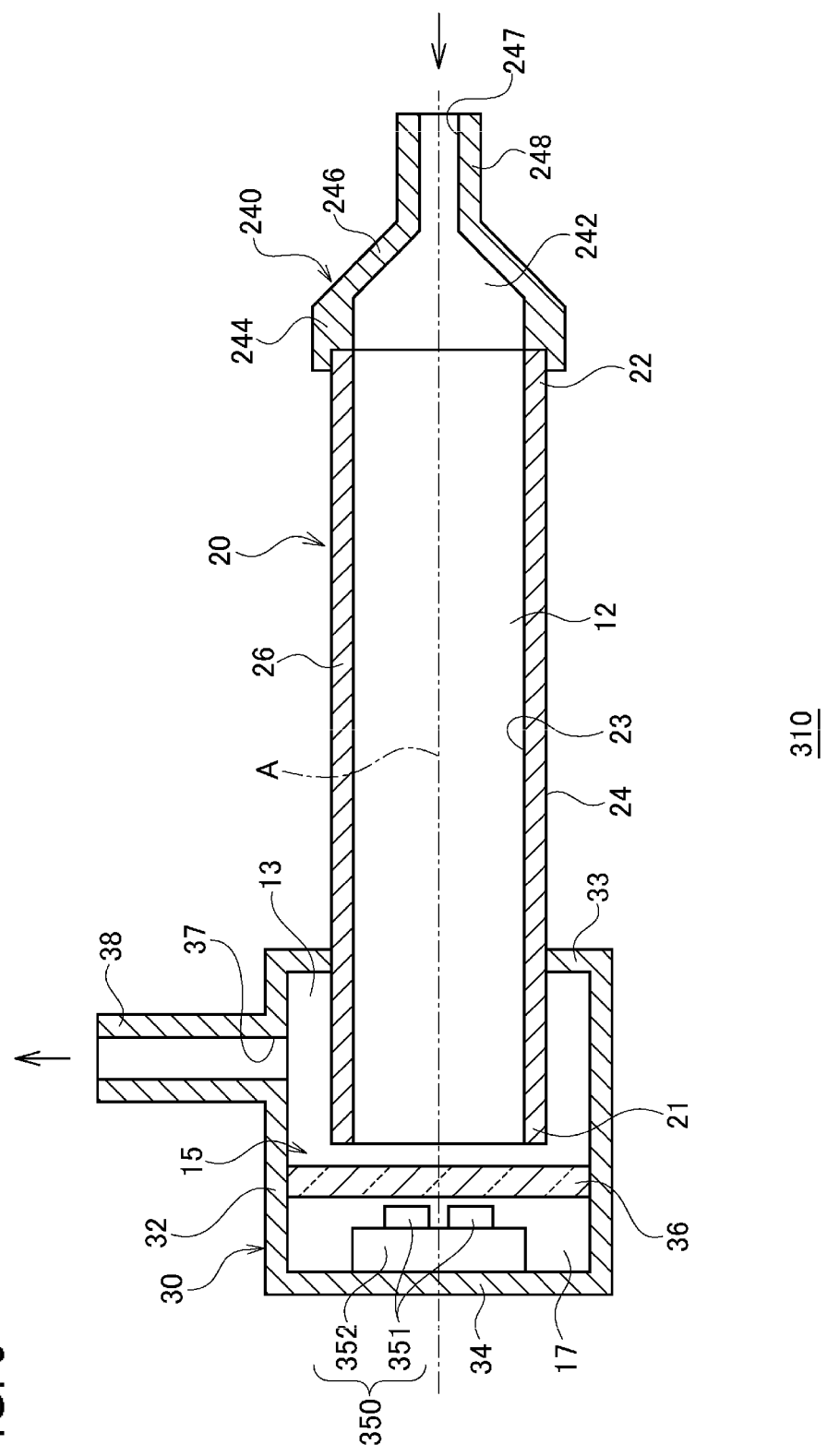
FIG. 9 is a cross-sectional view schematically showing a configuration of a fluid sterilization device according to a variation.

FIG. 9 is a cross-sectional view schematically showing a configuration of a fluid sterilization device 310 according to a fourth variation. The fluid sterilization device 310 differs from the second embodiment in that a light source 350 including a plurality of light emitting devices 351 is provided. A description of the fluid sterilization device 310 will be given below, highlighting the difference from the first embodiment.

The fluid sterilization device 310 includes the flow passage tube 20, the first housing 30, the inflow pipe 240, and the light source 350. The flow passage tube 20, the first housing 30, and the inflow pipe 240 are configured as in the second embodiment.

The light source 350 includes a plurality of light emitting devices 351 and a substrate 352. Each light emitting device 351 is configured similarly to the first light emitting device 51 or the second light emitting device 56. The plurality of light emitting devices 351 are provided on the substrate 352 and are oriented to irradiate the interior of the flow passage tube 20 with ultraviolet light from the first end 21.

For example, the plurality of light emitting devices 351 are arranged close together in the vicinity of the central axis A of the flow passage tube 20 and are arranged symmetrically around the central axis A. For example, the light source 350 may include four light emitting devices 351 and the four light emitting devices 351 are regularly arranged at equal distances from the central axis A. This causes the light source 350 to emit ultraviolet light having a relatively high intensity near the center of the cross-section of the processing passage 12 around the axial direction and a relatively low intensity radially outward. The light source 350 may include three or fewer light emitting devices 351 or five or more light emitting devices 351.

According to this variation, the light source 350 includes a plurality of light emitting devices 351 so that the fluid flowing in the processing passage 12 is irradiated with ultraviolet light of a higher intensity. By configuring the light intensity to be relatively higher near the center and relatively lower in the vicinity of the inner surface 23 to conform to the flow rate distribution inside the processing passage 12, the entirety of the fluid flowing in the processing passage 12 is irradiated with ultraviolet light effectively. Thus, according to this variation, the sterilization effect from ultraviolet irradiation is enhanced.

Described above is an explanation based on an exemplary embodiment. The embodiment is intended to be illustrative only and it will be understood by those skilled in the art that various design changes are possible and various modifications are possible and that such modifications are also within the scope of the present invention.

The fluid sterilization device according to the embodiments and variations described above is described as a device for irradiating the fluid with ultraviolet light so as to sterilize the fluid. In one variation, the inventive sterilization device may be used for a purification process that decomposes organic substance included in a fluid by using ultraviolet irradiation.

In the embodiments and variations above, a structure is shown in which the window that transmits ultraviolet light separates between the light source chamber and the straightening chamber. In a further variation, a partition wall that separates between the light source chamber and the straightening chamber may be provided and a window may be provided in a portion of the partition wall. In this case, the partition wall may be made of a material that does not transmit ultraviolet light. The partition wall may function as the opposing member opposing the end of the flow passage tube and form a gap with respect to the end of the flow passage tube.

In a further variation, an inflow pipe extending from the flow passage tube 20 in the radial direction may be provided instead of providing the inflow pipe 240 coaxial with the central axis A of the flow passage tube 20. In other words, the opening at the second end 22 of the flow passage tube 20 may be blocked and an inflow pipe extending from the side wall 26 in the vicinity of the second end 22 in the radial direction may be provided.

In a further variation, the fluid may be caused to flow in a direction opposite to the direction of flow illustrated in the embodiments and variations. In other words, the inflow port and the outflow port may be used the way around. For example, the fluid may be caused to flow in via the outflow port 37 and flow out via the inflow port 247 in the second embodiment shown in FIG. 7. In other words, the communication port 37 denoted by the reference numeral 37 may be used as the inflow port and the communication port denoted by the reference numeral 247 may be used as the outflow port.

In a further variation, the light source may have an adjustment mechanism for adjusting the intensity distribution of the ultraviolet light emitted by the light emitting device. The adjustment mechanism may include an optical device of a transmission type such as a lens or an optical device of a reflection type such as a concave mirror. The adjustment mechanism may shape the intensity distribution of the ultraviolet light output from the light source to conform to the speed distribution of the straightened flow by adjusting the intensity distribution of the ultraviolet light from the light emitting device. By providing the adjustment mechanism like this, ultraviolet light of an intensity distribution suited to the mode of flow of the fluid is radiated so that the sterilization effect is further increased.

It should be understood that the invention is not limited to the above-described embodiment, but may be modified into various forms on the basis of the spirit of the invention. Additionally, the modifications are included in the scope of the invention.

The invention claimed is:

1. A fluid sterilization device comprising:
   a flow passage tube having a first end and a second end opposite to the first end and defining a processing passage extending in an axial direction;
   a light source provided in a vicinity of the first end and radiating ultraviolet light from the first end toward the processing passage in the axial direction; and
   a housing that defines a straightening chamber encircling the first end from outside in a radial direction, wherein the straightening chamber includes a communication port that serves as an inlet or an outlet for a fluid flowing in the processing passage and communicates with the processing passage via a gap between the first end and an opposing member opposing the first end in the axial direction.

2. The fluid sterilization device according to claim 1, wherein
   at least a portion of the opposing member is made of a material that transmits the ultraviolet light from the light source and the light source is provided in a light source chamber defined by the housing and the opposing member.

3. The fluid sterilization device according to claim 1, wherein
   the opposing member is provided such that a dimension of the gap in the axial direction is uniform over an entire circumference of the first end.

4. The fluid sterilization device according to claim 1, further comprising:
   a connecting pipe connected to the communication port, wherein
   the connecting pipe extends in a direction intersecting a direction from the gap toward the communication port.

5. The sterilization device according to claim 1, wherein the communication port is provided at a position shifted from the gap in the axial direction.

6. The fluid sterilization device according to claim 1, wherein
the straightening chamber has a section that extends outside the fluid passage tube from the first end toward the second end in the axial direction.

7. The fluid sterilization device according to claim 1, wherein
the fluid passage tube is made of a material that reflects the ultraviolet light from the light source.

8. The fluid sterilization device according to claim 7, wherein
the housing is made of a material having a lower reflectivity for the ultraviolet light than the flow passage tube.

9. The fluid sterilization device according to claim 1, wherein
the flow passage tube has a projection that projects radially inward from the first end.

10. The fluid sterilization device according to claim 1, wherein
the light source includes at least one light emitting device that emits ultraviolet light and radiates ultraviolet light in a light distribution in which an ultraviolet light intensity near a center of a cross-section of the processing passage perpendicular to the axial direction is higher than an ultraviolet light distribution toward a circumference.

11. The fluid sterilization device according to claim 1, wherein
the light source is arranged such that an entirety of the ultraviolet light output from the light source in a range of half-power beam width is incident into the processing passage.

12. The fluid sterilization device according claim 1, further comprising:
a straightener for straightening the fluid flowing in the processing passage.

13. The fluid sterilization device according claim 1, wherein
the gap is formed to be narrower than the cross-sectional area of flow of the processing passage and the straightening chamber.

14. The fluid sterilization device according claim 1, wherein
the housing is a first housing, the straightening chamber is a first straightening chamber, the communication port is a first communication port, the gap is a first gap, and the opposing member is a first opposing member,
the fluid sterilization device further comprising:
a second housing that defines a second straightening chamber encircling the second end from outside in the radial direction, wherein
the second straightening chamber includes a second communication port that serves as an inlet or an outlet for a fluid flowing in the processing passage and communicates with the processing passage via a second gap between the second end and a second opposing member opposing the second end in the axial direction.

15. The fluid sterilization device according claim 14, wherein
the light source is a first source,
the fluid sterilization device further comprising:
a second light source provided in a vicinity of the second end and radiating ultraviolet light from the second end toward the processing passage in the axial direction.

16. The fluid sterilization device according to claim 15, wherein
the light source chamber is a first light source chamber, and
at least a portion of the second opposing member is made of a material that transmits the ultraviolet light from the second light source and the second light source is provided in a second light source chamber defined by the second housing and the second opposing member.

17. The fluid sterilization device according claim 14, wherein
the second opposing member is a reflector that reflects the ultraviolet light output from the light source.

18. The fluid sterilization device according claim 1, further comprising:
a funnel-shaped inflow pipe connected with the second end, wherein
the communication port serves as the outlet.

* * * * *